US009603957B2

(12) United States Patent
Kirkwold et al.

(10) Patent No.: US 9,603,957 B2
(45) Date of Patent: Mar. 28, 2017

(54) MULTIPLE PUMP EVAPORATIVE MEDIA SYSTEM

(71) Applicant: DRI-STEEM Corporation, Eden Prairie, MN (US)

(72) Inventors: Mark Allen Kirkwold, Shakopee, MN (US); Cole K. Farley, Long Lake, MN (US); James M. Lundgreen, Lakeville, MN (US)

(73) Assignee: Dri-Steem Corporation, Eden Prairie, MN (US)

( * ) Notice: Subject to any disclaimer, the term of this patent is extended or adjusted under 35 U.S.C. 154(b) by 139 days.

(21) Appl. No.: 14/598,768

(22) Filed: Jan. 16, 2015

(65) Prior Publication Data

US 2015/0204552 A1    Jul. 23, 2015

Related U.S. Application Data

(60) Provisional application No. 61/928,775, filed on Jan. 17, 2014, provisional application No. 61/928,740, (Continued)

(51) Int. Cl.
*B01F 3/04* (2006.01)
*A61L 2/10* (2006.01)
(Continued)

(52) U.S. Cl.
CPC ............ *A61L 2/10* (2013.01); *B01F 3/04021* (2013.01); *B01F 3/04078* (2013.01); *B01F 3/04085* (2013.01); *F24F 5/0035* (2013.01); *F24F 6/043* (2013.01); *F25B 39/02* (2013.01); *F25B 39/028* (2013.01); *F25D 7/00* (2013.01);
(Continued)

(58) Field of Classification Search
CPC .... B01F 3/04; B01F 3/04007; B01F 3/04021; B01F 3/04078; B01F 3/04085
USPC .... 261/94, 97, 98, 26, 34.1, 36.1, 72.1, 115, 261/118, DIG. 3, DIG. 43
See application file for complete search history.

(56) References Cited

U.S. PATENT DOCUMENTS 2,160,549 A * 5/1939 Kurth .................. F24F 6/04
                                                  261/98
6,338,471 B1 * 1/2002 Imsdahl .................. F28D 5/00
                                                  261/27
(Continued)

FOREIGN PATENT DOCUMENTS

WO    WO 01/79771 A1    10/2001
WO    WO 2007/055838 A2    5/2007

*Primary Examiner* — Robert A Hopkins
(74) *Attorney, Agent, or Firm* — Merchant & Gould P.C.

(57) ABSTRACT

An evaporative media system having multiple media stages each served by a separate pump is disclosed. In one aspect, the evaporative media system has a first media stage and a second media stage. A first pump is provided that is configured to deliver water from the first compartment of the water storage tank to the first media stage. Additionally, a second pump is provided that is configured to deliver water from the first compartment of the water storage tank to the second media stage. Additional media stages and pumps may be provided as well. The disclosed configuration eliminates the need for individual staging valves, provides a higher level of operational redundancy, reduces electrical consumption, and can be provided at a lower cost, as compared to many existing systems.

16 Claims, 5 Drawing Sheets

Related U.S. Application Data filed on Jan. 17, 2014, provisional application No. 61/928,764, filed on Jan. 17, 2014, provisional application No. 61/928,784, filed on Jan. 17, 2014, provisional application No. 61/928,800, filed on Jan. 17, 2014.

(51) Int. Cl.

| | | |
|---|---|---|
| *F24F 5/00* | (2006.01) | |
| *F28C 3/08* | (2006.01) | |
| *F25B 39/02* | (2006.01) | |
| *F25D 7/00* | (2006.01) | |
| *G05D 9/12* | (2006.01) | |
| *F24F 6/04* | (2006.01) | |
| *F24F 1/00* | (2011.01) | |

(52) U.S. Cl.
CPC ............... *F28C 3/08* (2013.01); *G05D 9/12* (2013.01); *F24F 2001/0088* (2013.01); *Y02B 30/545* (2013.01); *Y10T 137/0318* (2015.04); *Y10T 137/7303* (2015.04)

(56) References Cited

U.S. PATENT DOCUMENTS

| | | |
|---|---|---|
| 6,513,339 B1 | 2/2003 | Kopko |
| 7,165,410 B2 | 1/2007 | Carr et al. |
| 7,712,300 B2 | 5/2010 | Bevilacqua et al. |
| 7,765,827 B2 * | 8/2010 | Schlom ............... F24F 5/0007 62/309 |
| 8,496,732 B2 | 7/2013 | Culp et al. |
| 2001/0054354 A1 * | 12/2001 | Baudat ............... B01D 47/06 95/214 |
| 2004/0093882 A1 | 5/2004 | Sangwan et al. |
| 2007/0101746 A1 | 5/2007 | Schlom et al. |
| 2011/0030552 A1 | 2/2011 | Fong et al. |
| 2012/0118148 A1 | 5/2012 | Culp et al. |
| 2012/0118155 A1 | 5/2012 | Claridge et al. |
| 2013/0333407 A1 | 12/2013 | Jarvis |
| 2015/0204553 A1 | 7/2015 | Kirkwold et al. |
| 2015/0204554 A1 | 7/2015 | Farley et al. |
| 2015/0204588 A1 | 7/2015 | Lundgreen et al. |
| 2015/0205305 A1 | 7/2015 | Kirkwold et al. |
| 2015/0260419 A1 | 9/2015 | Muenzberg et al. |

* cited by examiner

FIG. 3

MULTIPLE PUMP EVAPORATIVE MEDIA SYSTEM

CROSS-REFERENCE TO RELATED APPLICATIONS

This application claims priority to U.S. Application Ser. No. 61/928,740, filed on Jan. 17, 2014, entitled "Evaporative Cycles of Concentration Control," the entirety of which is incorporated by reference herein. This application also claims priority to U.S. Application Ser. No. 61/928,764, filed on Jan. 17, 2014, entitled "Circulation and Drain System," the entirety of which is incorporated by reference herein. This application claims priority to U.S. Application Ser. No. 61/928,775 filed on Jan. 17, 2014, entitled "Staging Control for an Evaporative Media System," the entirety of which is incorporated by reference herein. This application also claims priority to U.S. Application Ser. No. 61/928,784, filed on Jan. 17, 2014, entitled "Staging Control for an Evaporative Media System," the entirety of which is incorporated by reference herein. This application also claims priority to U.S. Application Ser. No. 61/928,800, filed on Jan. 17, 2014, entitled "Staged Dry Out Control for Evaporative Media Systems," the entirety of which is incorporated by reference herein.

BACKGROUND

Evaporative media systems, for example direct evaporative coolers, are frequently used in commercial and industrial HVAC systems, including applications for data centers and power plant turbine inlet cooling. Evaporative media systems consume less energy than conventional cooling equipment and are increasingly being used to supplement and occasionally replace conventional cooling equipment. In operation, evaporative media systems use the enthalpy of vaporization of water as a means to cool and humidify air. Typically, this is accomplished by flowing air directly through a media wetted with water. As air passes through the wetted media, water evaporates by taking energy from the air to vaporize the water. Accordingly, the air temperature exiting the wetted media is reduced and the humidity is increased while the energy or enthalpy of the exiting air remains the same as the entering air. This type of a process is often referred to as adiabatic cooling.

Evaporative media systems typically use a water pump to transfer water in a tank below the media to the top of the media. The water flows down through the media where a portion of the water evaporates and the rest of the water drains out the media bottom into the tank below. The water continues to be re-circulated using the water pump, or re-circulation pump, with make-up water added to replace the evaporated water. Tank water is periodically drained and replaced with additional make-up water as the tank water concentrates to control and minimize scale fouling, biological fouling and corrosion.

Large commercial and industrial evaporative media systems usually have multiple cooling capacities to accommodate the varying cooling demands of the application. This is accomplished by wetting only portions, or stages, of the evaporative cooler media. There may be two or more stages on a single evaporative cooler with multiple cooling capacities. Typically, a single re-circulation pump is connected to a manifold with multiple staging valves and a water line to each stage. To wet a stage the staging valve is energized while the re-circulation pump is running, thus opening and sending water to that stage. Staging valves are opened and closed as needed to match the cooling demands of the application.

However, there are several problems with such single re-circulation pump and multiple staging valve designs. For example, staging valves can fail and are susceptible to plugging and/or sticking since they are a solenoid design and not a full port valve. Additionally, if the single re-circulation pump fails the evaporative cooler becomes inoperable. A single re-circulation pump is also necessarily oversized for much of the operating time which wastes electricity and heats the water. The pump must flow enough water to wet all the stages, however, it continues to pump at full power with fewer than all stages wetted. A further issue is that the staging valves must have a high flow rate and be suitable for wet environments, which makes them costly. When the large pump and manifold costs are added to the valves, the total cost can become excessive. Improvements are desired.

SUMMARY

An evaporative media system having a water storage tank having a first compartment is disclosed. In one aspect, the evaporative media system has a first media stage and a second media stage. A first pump may be provided that is configured to deliver water from the first compartment of the water storage tank to the first media stage. Additionally, a second pump may be provided that is configured to deliver water from the first compartment of the water storage tank to the second media stage. A third pump associated with a third media stage may also be provided in the evaporative media system. In one embodiment, the pumps have the same flow capacity while in another embodiment, the pumps have flow capacities that are different from each other.

DESCRIPTION OF THE DRAWINGS

Non-limiting and non-exhaustive embodiments are described with reference to the following figures, which are not necessarily drawn to scale, wherein like reference numerals refer to like parts throughout the various views unless otherwise specified.

DETAILED DESCRIPTION

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

General Evaporative Media System Description

Figure 1:
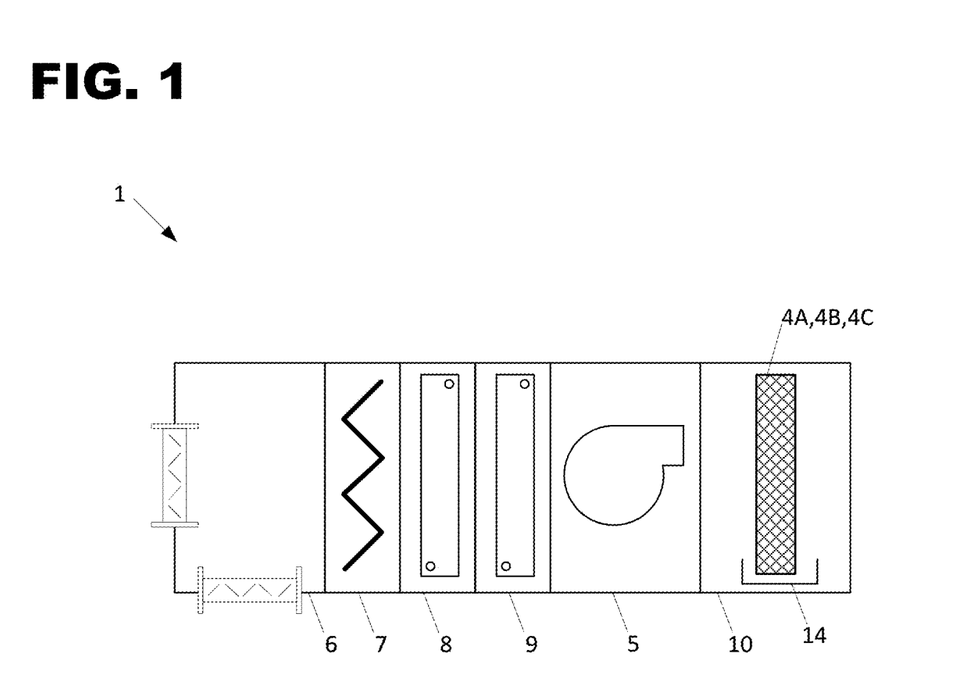
FIG. 1 is a schematic side view of an air handling system having features that are examples of aspects in accordance with the principles of the present disclosure.
Figure 2:
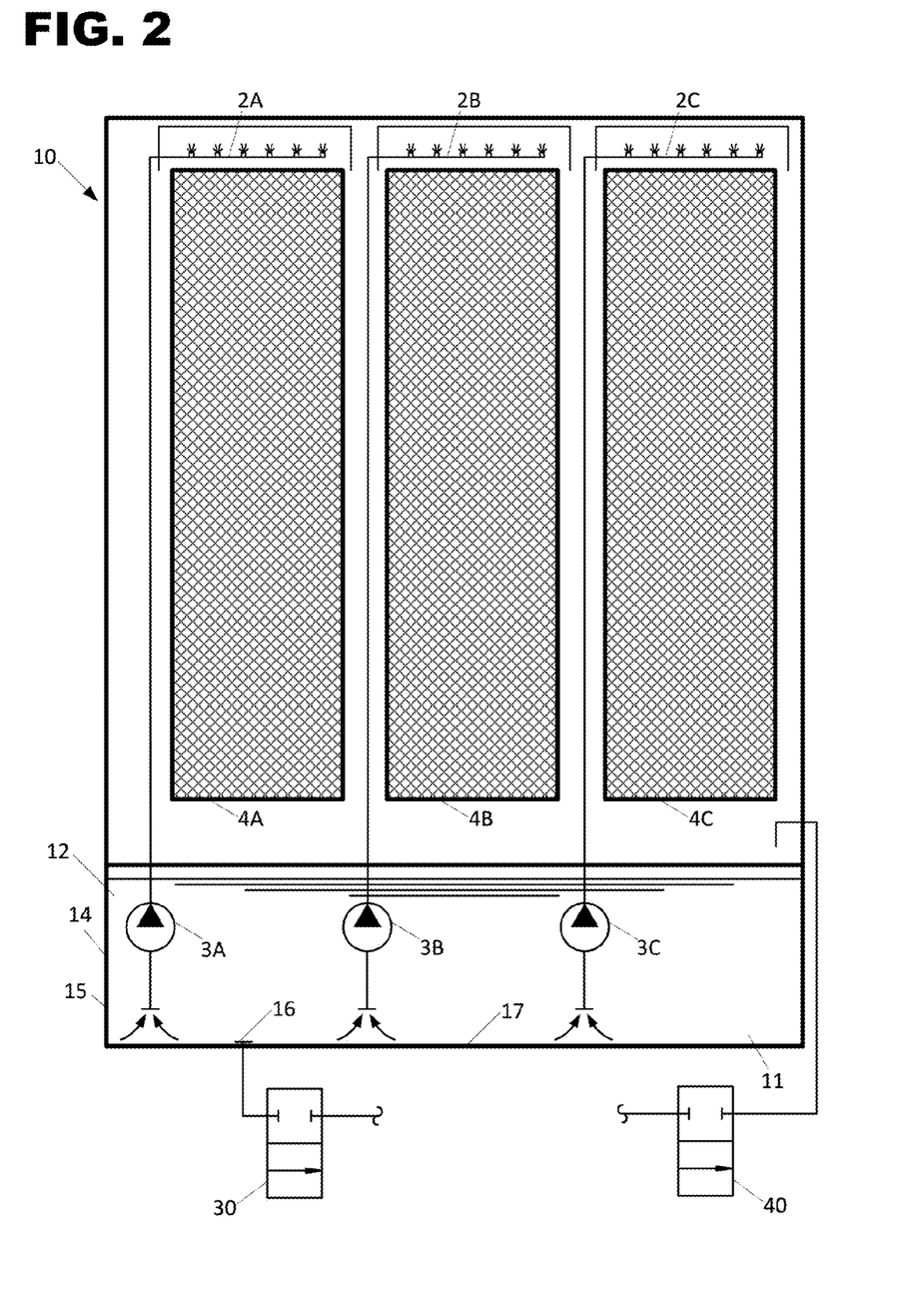
FIG. 2 is a schematic end view of a three stage evaporative media system having features that are examples of aspects in accordance with the principles of the present disclosure, the evaporative media system being usable in the air handling system shown in FIG. 1.
Figure 2A:
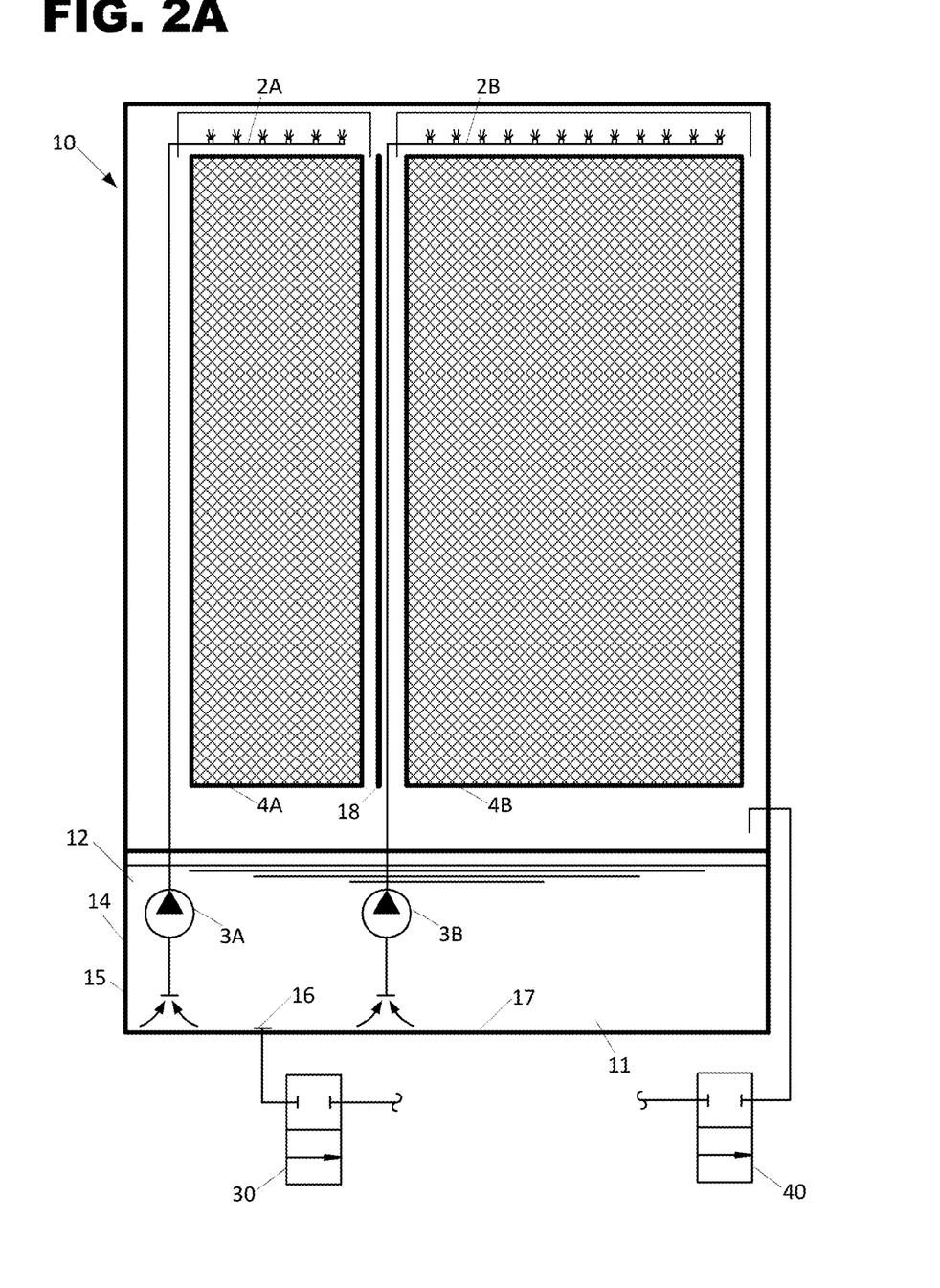
FIG. 2A is a schematic end view of a two stage evaporative media system having features that are examples of aspects in accordance with the principles of the present disclosure, the evaporative media system being usable in the air handling system shown in FIG. 1.
Figure 2B:
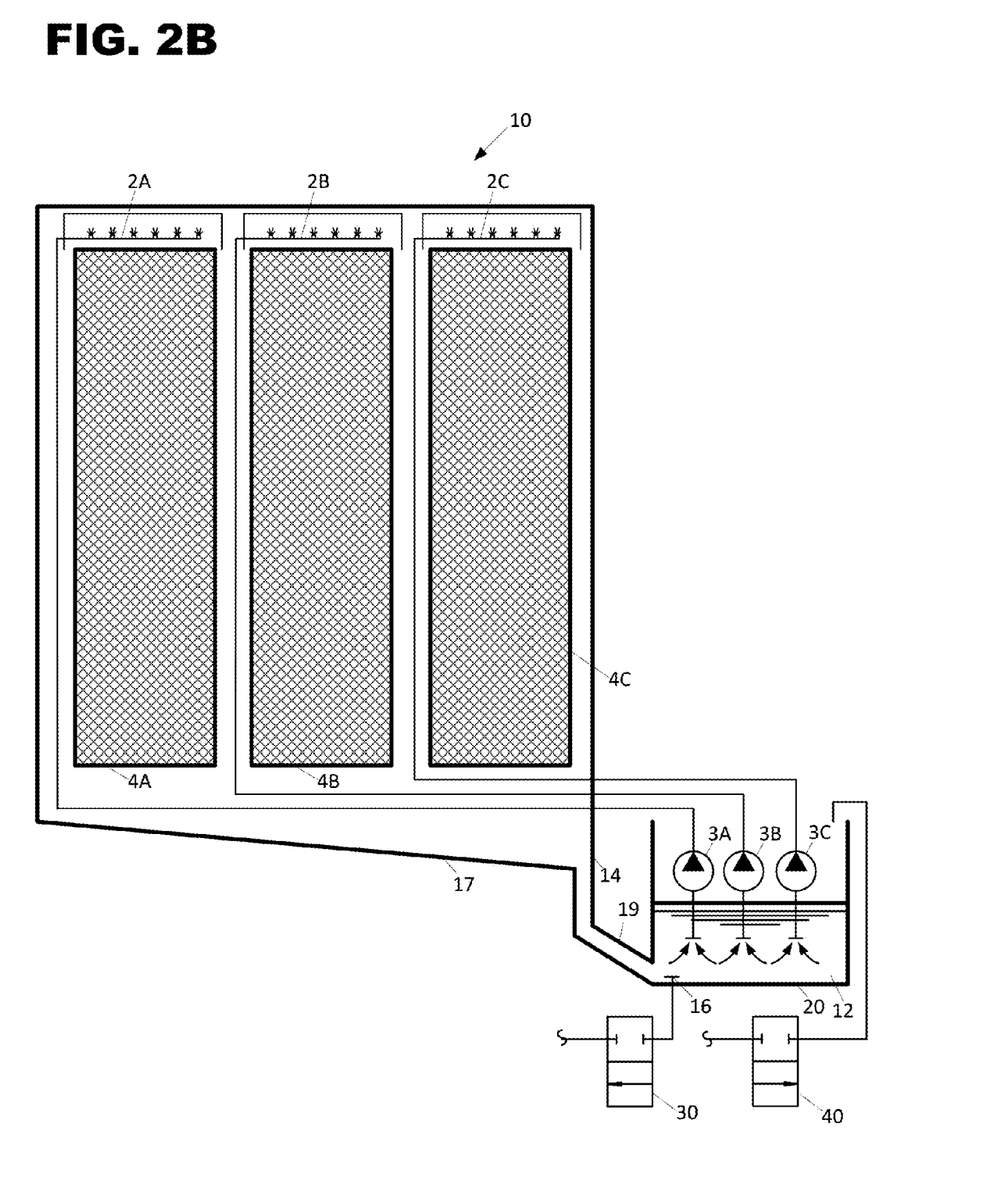
FIG. 2B is a schematic end view of a three stage evaporative media system having features that are examples of aspects in accordance with the principles of the present disclosure, the evaporative media system being usable in the air handling system shown in FIG. 1.

Referring to FIG. 1, an air handling system 1 comprising an evaporative media system 10 is shown. FIGS. 2, 2A, and 2B show three and two stage versions of the evaporative media system 10 in additional detail. As shown, the air handling unit may be additionally provided with a supply fan 5, a damper section 6, a filter 7, a heating coil 8, and a cooling coil 9. It should be understood that various other components and alternative configurations may be applied to air handling system 1 without departing from the concepts disclosed herein. In operation, the supply fan 5 draws air through the evaporative media system 10 to result in adiabatically cooled air when the evaporative media system 10 is activated.

In one aspect, the evaporative media system 10 shown at FIGS. 2, 2A, and 2B includes an evaporator tank 14 having a sidewall 15 and a bottom side 17 that together define an interior volume 11 for holding a fluid 12, such as water. As shown, the tank 14 defines a single compartment with a single interior volume 11 for holding a fluid 12. The sidewall 15 may have various cross-sectional shapes as dictated by the requirements of the evaporator and air handling unit, for example square, rectangular, and circular cross-sectional shapes. The bottom side 17 may also be provided with various shapes to accommodate the perimeter defined by the sidewall 15.

The storage tank 14 may be provided with a drain opening 16 located in one of the bottom side 17 and the sidewall 15. In the particular embodiment shown, the drain opening 16 is provided at the bottom side 17 of the tank 14. In one aspect, a drain valve 30 is provided to selectively drain water from the tank 14 while a fill valve 40 is provided to selectively add water to the tank 14. The drain and fill valves 30, 40 may be provided as automatic control valves operated by a controller, such as electronic controller 500 discussed below.

As presented, evaporative media system 10 also includes a plurality of media stages 4A, 4B, 4C through which air is drawn via the operation of fan 5. FIGS. 2 and 2B show a three stage system having stages 4A, 4B, 4C of a generally equal size and capacity while FIG. 2A shows a two stage system having a first stage 4A and a second stage 4B that is about double the size of the first stage 4A. It should be appreciated that the evaporative media system 10 may include fewer or more media stages of same or different sizes without departing from the concepts disclosed herein. Furthermore, each media stage may include multiple subsections of media. As shown, each media section 4A, 4B, 4C is separated from the other by a gap, or alternatively a frame or barrier 18 (shown at FIG. 2A), to prevent moisture from communicating from one section to the other. This configuration allows for an individual media section to be dry out without being subjected to wicking moisture from an adjacent section.

Each individual media stage 4A, 4B, 4C is shown as being provided with an individual corresponding distribution pump 3A, 3B, 3C. A spray distribution apparatus 2A, 2B, 2C is in fluid communication with each pump 3A, 3B, 3C such that each pump 3A, 3B, 3C can deliver fluid 12, such as water, from the storage tank 14 to a spray distribution apparatus 2A, 2B, 2C to wet the associated media stage 4A, 4B, 4C.

The output flow capacities of each of the pumps 3A, 3B, 3C may the same as each other or different from each other. For example, in the embodiment shown in FIG. 2A, the second distribution pump 3B is configured to have twice the flow capacity as the first distribution pump 3A as the second media stage 4B is twice the size of the first media stage 4A. For the embodiment shown in FIG. 2, the flow capacities of each pump 3A, 3B, 3C are the same. Other configurations are possible.

In one embodiment, the same pump size and model is used for each of pumps 3A, 3B, and/or 3C, even where the media stages are of different sizes/capacities. The desired pump flow rate for a media stages 4A and 4B can determined by the width and depth of the media multiplied by a flow rate per square foot, for example 1.5 gallons per minute (gpm) per square foot. Accordingly, as media stage 4B is shown as having twice the width of media stage 4A, media stage 4B would require a flow rate that is twice the flow rate of that required by media stage 4A. The desired different flow rates can be achieved by choosing the appropriate quantity and diameter of holes in the distribution header 2A, 2B for the specific pump flow curve and head pressure. In other words, with the appropriate amount of restriction, the pump 3A will provide the desired flow rate for media stage 4A, and with a less amount of restriction, the pump 3B, which is the same as pump 3A, will provide the desired higher flow rate for the media stage 4B.

As should be appreciated, the pump being used for pump 3A, 3B can be selected to provide sufficient flow rate for the largest stage of the largest system (e.g. stage 4B). By knowing the flow rate, head pressure, losses through piping and the pump curve, the appropriate quantity and diameter of holes in the distribution header 2A, 2B, 2C can be calculated. One suitable pump for pumps 3A, 3B, and 3C is a Little Giant F-Series F10-1200 (manufactured by Franklin Electric of Oklahoma City, Okla.). This type of pump has a wet rotor design without a shaft seal to separate the motor from the pump wherein water circulates around the armature.

In operation, when a pump 3A, 3B, 3C is activated (e.g. turned on or modulated to a speed greater than zero), the associated media stage 4A, 4B, 4C is wetted with fluid 12. When a media stage 4A, 4B, 4C is being actively wetted with water, for example when the associated pump 3A, 3B, 3C is in operation, that media stage 4A, 4B, 4C can be referred to as being activated. Likewise, when a media stage 4A, 4B, 4C is not being actively wetted with water, for example when the associated pump 3A, 3B, 3C is shut off and not in operation, that media stage 4A, 4B, 4C can be referred to as being deactivated.

The above described configuration utilizes relatively small, efficient re-circulation pumps 3A, 3B, 3C fitted for each stage with no manifold and no staging valves. Since relatively small individual pumps are used for each stage, electrical consumption and water heating is reduced, especially when operating with fewer than all stages wetted. The peak electrical demand from multiple, smaller pumps is also reduced in comparison to a single larger pump sized to meet the total capacity of the smaller pumps. Additionally, the cost of several small pumps is less than the cost of a single large pump, manifold and multiple staging valves. Since staging valves are completely eliminated, this configuration also removes any risk of valve failure, plugging or sticking. The system 10 also provides some level of redundancy in that if a staging pump fails operation, the system 10 can still continue to operate at a reduced output with the remaining staging pumps. Additionally, the use of multiple pumps is advantageous in a system where peak demand load must be reduced since the system can still be operated at a reduced capacity with one or more of the pumps turned off.

Referring to FIG. 2B, the evaporative media system 10 is shown with an external reservoir 20 which is connected to the evaporator tank 14 via a passageway or conduit 19. As shown, the bottom side 17 of the evaporator tank 14, configured here as a drain pan 14, is sloped towards conduit 19 such that all collected fluid 12 is drained into the external reservoir 20. In one example, each of the pumps 3A, 3B, 3C are placed within the external reservoir 20 (instead of a tank 14) and are provided with piping to each of the evaporator stages 2A, 2B, 2C. The drain 16, the drain valve 30, and the fill valve 40 can be configured to drain and deliver fluid 12 to the external reservoir 20 rather than the tank 14.

Control System

Figure 3:
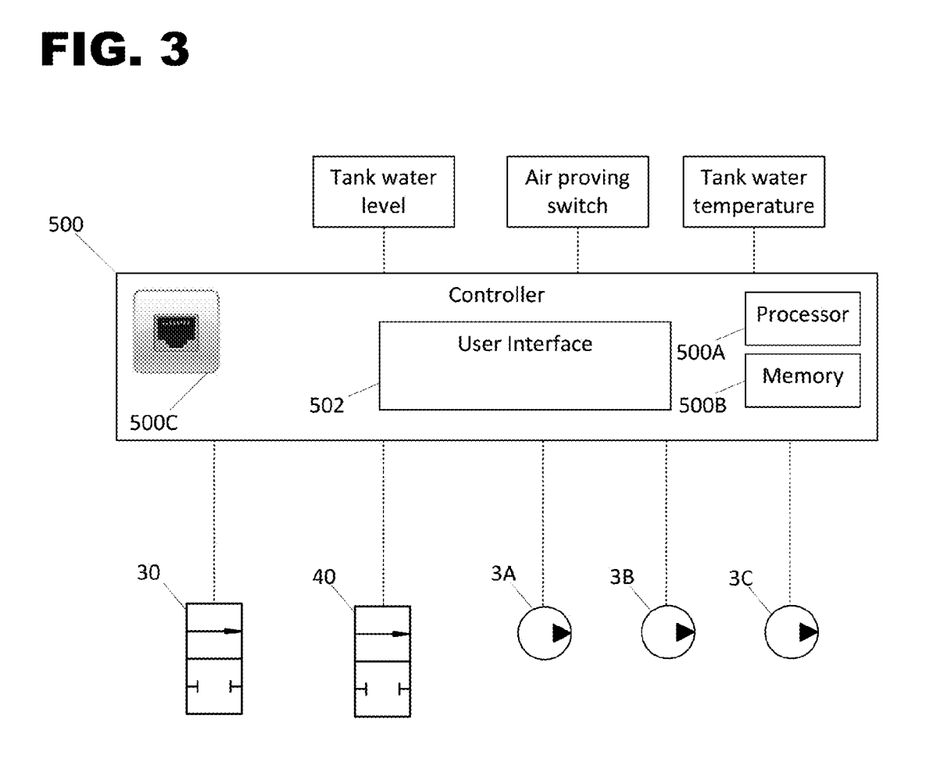
FIG. 3 is a schematic view of a control system usable with the evaporative media system and air handling unit shown in FIG. 1.

Referring to FIG. 3, the evaporative media system may also include an electronic controller 500. The electronic controller 500 is schematically shown as including a processor 500A and a non-transient storage medium or memory 500B, such as RAM, flash drive or a hard drive. Memory 500B is for storing executable code, the operating parameters, and the input from the operator user interface 502 while processor 500A is for executing the code. The electronic controller is also shown as including a transmitting/receiving port 500C, such as an Ethernet port for two-way communication with a related WAN/LAN or to another controller associated with the automation system. A user interface 502 may be provided to activate and deactivate the system, allow a user to manipulate certain settings or inputs to the controller 500, and to view information about the system operation.

The electronic controller 500 typically includes at least some form of memory 500B. Examples of memory 500B include computer readable media. Computer readable media includes any available media that can be accessed by the processor 500A. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the processor 500A.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

Electronic controller 500 is also shown as having a number of inputs/outputs that may be used for implementing desired operational modes of the evaporative media system 10 and/or the air handling system 1. For example, electronic controller 500 provides outputs for commanding individual evaporator stage pumps 3A, 3B, 3C such that they can be staged as needed to meet the output demands of the system 10 (e.g. a leaving air temperature or relative humidity set point). Controller 500 may also provide outputs for controlling the tank fill valve 40, and an output for controlling the tank drain valve 30. Status inputs can be provided for each of the aforementioned control components as well. Additionally, inputs for entering and leaving air temperature and humidity, outdoor air temperature and humidity, tank water level, tank water temperature (which can serve as a proxy for entering and leaving air wet bulb temperatures), and an airflow switch (or a fan status input signal) may be provided as well. The controller 500 can also include the necessary inputs and outputs for desirable operation of the remaining components of the air handling system 1, for example, inputs and outputs to operate the fan 5, damper section 6, and the coils 8, 9.

In one aspect, the controller 500 may be programmed to execute a staging control process whereby selected media stages are activated to meet a set point, such as a leaving air temperature or relative humidity set point. One example of a staging approach usable with the disclosed system and controller 500 is described in concurrently filed United States Patent Application Ser. No. 61/928,784 entitled "Staging Control for an Evaporative Media System," filed on Jan. 17, 2013 , the entirety of which is incorporated by reference herein.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the disclosure.

What is claimed is:

1. An evaporative media system comprising:
  a. a water storage tank having a first compartment;
  b. a first media stage;
  c. a second media stage;
  d. a first pump configured to deliver water from the first compartment of the water storage tank to the first media stage; and
  e. a second pump configured to deliver water from the first compartment of the water storage tank to the second media stage;
  f. wherein the first and second pumps are at least partially located within the first compartment and have different flow capacities.

2. The evaporative media system of claim 1, further comprising:
  a. a third media stage; and
  b. a third pump configured to deliver water from the first compartment of the water storage tank to the third media stage.

3. The evaporative media system of claim 1, further comprising:
  a. a controller for selectively activating and deactivating the first and second pumps.

4. The evaporative media system of claim 3, wherein:
   a. the controller is an electronic controller configured to selectively activate and deactivate the first and second pumps to maintain a leaving air temperature or relative humidity set point.

5. The evaporative media system of claim 2, further comprising:
   a. a controller for selectively activating and deactivating the first, second, and third pumps.

6. The evaporative media system of claim 5, wherein:
   a. the controller is an electronic controller configured to selectively activate and deactivate the first, second, and third pumps to maintain a leaving air temperature or relative humidity set point.

7. The evaporative media system of claim 1, wherein the water storage tank is configured as an external reservoir that is connected to a drain pan via a conduit, the drain pan being located below the first and second media stages.

8. The evaporative media system of claim 1, wherein the second pump has a flow capacity that is about twice the flow capacity of the first pump.

9. The evaporative media system of claim 1, wherein the evaporative media system is configured for installation in an air handling unit having a supply fan.

10. An air handling system comprising:
    a. a water storage tank having a first compartment;
    b. a first media stage;
    c. a second media stage;
    d. a first pump configured to deliver water from the first compartment of the water storage tank to the first media stage;
    e. a second pump configured to deliver water from the first compartment of the water storage tank to the second media stage, wherein the first and second pumps have different flow capacities; and
    f. a supply fan having housing defining an inlet and an outlet, wherein the first and second media stages are located within the housing and the supply fan is configured to draw air through the inlet, through the first and second media stages, and out of the outlet.

11. The air handling system of claim 10, further comprising:
    a. a third media stage; and
    b. a third pump configured to deliver water from the first compartment of the water storage tank to the third media stage.

12. The air handling system of claim 10, further comprising:
    a. a controller for selectively activating and deactivating the first and second pumps and the fan.

13. The air handling system of claim 12, wherein:
    a. the controller is an electronic controller configured to selectively activate and deactivate the first and second pumps to maintain a leaving air temperature or relative humidity set point.

14. The air handling system of claim 11, further comprising:
    a. a controller for selectively activating and deactivating the first, second, and third pumps and the fan.

15. The air handling system of claim 14, wherein:
    a. the controller is an electronic controller configured to selectively activate and deactivate the first, second, and third pumps to maintain a leaving air temperature or relative humidity set point.

16. The air handling system of claim 10, wherein the second pump has a flow capacity that is about twice the flow capacity of the first pump.

* * * * *